United States Patent [19]

Lapidus

[11] Patent Number: 4,503,116
[45] Date of Patent: Mar. 5, 1985

[54] DENTAL ADHESIVE DEVICE AND METHOD OF PRODUCING SAME

[75] Inventor: Herbert Lapidus, Ridgefield, Conn.

[73] Assignee: Combe Incorporated, White Plains, N.Y.

[21] Appl. No.: 508,381

[22] Filed: Jun. 29, 1983

Related U.S. Application Data

[63] Continuation-in-part of Ser. No. 236,889, Feb. 23, 1981, abandoned, and a continuation-in-part of Ser. No. 346,640, Feb. 8, 1982, abandoned.

[51] Int. Cl.$^3$ .................................................. B32B 5/26
[52] U.S. Cl. ................................. 428/286; 156/272.2; 156/275.7; 156/327; 428/290; 428/299; 428/300; 428/523; 433/168; 433/180
[58] Field of Search ............... 428/220, 286, 290, 299, 428/300, 500, 523, 224; 433/168, 180, 199; 156/272.2, 275.7, 527

[56] References Cited

U.S. PATENT DOCUMENTS

| | | | |
|---|---|---|---|
| 2,978,812 | 4/1961 | Rosenthal | 433/199 |
| 3,868,340 | 2/1975 | Keegan et al. | 260/17.4 ST |
| 3,990,149 | 11/1976 | Nedwig | 433/180 |

OTHER PUBLICATIONS

*Handbook of Adhesives*, Second Edition, Van Nostrand Reinhold Co., 1977, pp. 797-805.

Primary Examiner—Paul J. Thibodeau
Attorney, Agent, or Firm—Roland T. Bryan

[57] ABSTRACT

A new dental adhesive device to hold and cushion prosthetic devices in the human mouth is made as a laminate of webs which are bonded together by thermoplastic ethylene oxide polymer. The dental adhesive exemplified is produced by continuously applying thermoplastic ethylene oxide polymer between moving webs of cellulose acetate fibers, and then passing said webs in superimposed relationship between a pair of dry heated calendar rolls for thermoplastically bonding said web into a unitary structure. A dry water-activated adhesive material such as sodium alginate may be admixed with the thermoplastic ethylene oxide polymer and applied to the moving webs before passing between the calendar rolls. It is also contemplated that the synthetic fibers be applied to the webs so as to extend transversely through the webs with the free ends of the fibers from each web being entangled so as to be mechanically interlocked.

17 Claims, 6 Drawing Figures

DENTAL ADHESIVE DEVICE AND METHOD OF PRODUCING SAME

This is a continuation-in-part of application Ser. No. 236,889 filed Feb. 23, 1981, now abandoned, and a continuation-in-part of application Ser. No. 346,640, filed Feb. 8, 1982, now abandoned.

The present invention relates to a device for holding in place a prosthetic device in the human mouth and a method of producing same.

BACKGROUND OF THE INVENTION

Various denture fixative agents are known which swell in contact with water or saliva thus forming gel-like masses. These masses fill the space between the undersurfaces of the denture plate and the mouth tissue to effect a suction coupling. The agents have been provided in the form of films, powders and pastes which are placed on the wettened undersurfaces of the dental prosthetic plates. Certain polymers of ethylene oxide are reputed to have excellent fixative properties as seen in U.S. Pat. No. 2,978,812. Such fixative agents, however, have inherent disadvantages. Their uniformity depends on the care in which they are applied by the user to the underside of the denture plate. Moreover, due to saliva, such agents frequently dilute rapidly resulting in insufficient viscosity to form a good seal, and thereby limiting the effectiveness of said agents to a short duration. Finally, the manufacture of such agents is relatively expensive in that additives must be mixed with the basic agent to improve its flow properties, viscosity and tackiness.

Alternatively, there is known a dental adhesive in which there is a compressed fiber mat containing sodium alginate, a dry adhesive, which swells under the action of moisture in the mouth, as described in U.S. Pat. No. 3,990,149. That patent describes the manufacture of a dental adhesive in which sodium alginate is deposited as a dry powder on a non woven web having thermoplastic fibers. Water is then added so as to produce a semi-hydrated state which causes the second web of non woven web material to temporarily adhere to the other web by the resulting sticky wetted alginate. This material is then dried by passing it between heated rollers which also causes the thermoplastic fibers of the non woven mates to be permanently bonded to each other and thus to become a unitary piece. The products of the prior art adhesive manufacturing methods described have the disadvantage of being non uniformly bonded and often short-lived in their adhesiveness. Moreover, the systems of the '149 patent require very expensive and careful quality controls which often result in undetected products of poor quality. Moreover, the aforesaid method requires the use of expensive and time consuming drying ovens. Further, the product deleteriously releases loose fibers in the mouth of the user.

THE INVENTION

The present invention is a superior product which provides a resilient adhesive device of thermally laminated fabrics optionally having a water activated adhesive uniformly dispersed therebetween. Said product is suitable for use in the human mouth between a denture and the soft gum tissues. The invention includes a method for manufacturing said device which more economically produces a high quality product and which avoids the extremely careful controls required in prior art methods.

The new dental adhesive is a dry heat and pressure consolidated laminate comprising webs having a carrier portion with fibers bonded together by an interposed layer of ethylene oxide polymer, preferably in a powdered form, which has been thermoplastically formed to bond the fibers. The ethylene oxide polymer powder has been known as a dry water-activated adhesive, however the invention contemplates advantageously using its thermoplastic properties to make a better laminate for use in the mouth and to also use its recognized water activated adhesive properties to improve the laminate's denture fixative abilities. Moreover, the fixative properties may be improved by admixing the ethylene oxide polymer with another dry water-activated adhesive material to promote the formation of a gel-like adhesive mass between the denture plate and the mouth tissue.

The webs of the laminate may range from woven napped material, to an unwoven fiber or web such as a light polypropylene scrim or a cellulose paper, or to an unwoven fiber or web with cellulose acetate fibers bonded to said unwoven web as by needle punching. The new method of producing said new device consists essentially in progressively feeding one of said fiber faced webs over spaced feed rolls, while progressively depositing the ethylene oxide polymer binder together, if desired, with a dry water-activated adhesive in powder form to the opposite surface of said web. The so coated web is then fed together with a second but uncoated such web in superimposed relation, with said powder coating between them, under a guide roll and then between a pair of heated calendar rolls, heated to about 210° F., for heating and pressure consolidation of the resultant laminated assembly. The resultant laminated assembly is a dry manufactured dental adhesive laminate which has improved mechanical properties and when used will form a good seal between the gum and denture plate for long durations.

It is also contemplated that the synthetic fibers be applied to the webs so as to extend transversely through the webs. With the free ends of the fibers from each respective web thereby being caused to intermingle, an additional step of needle punching is employed to entangle and mechanically interlock the respective ends. Such a step may be employed after the webs have passed over the idler roll 26 and before they advance between the heated calendar rolls 27, 28. In this manner, even greater bonding between the webs is achieved by coupling the mechanical bonding of the fibers with that provided by the polymer binder and by the dry water-activated adhesive.

The invention may be more completely understood by the following detailed description and the drawings of the preferred embodiment referred to therein.

BRIEF DESCRIPTION OF THE DRAWINGS

In the accompanying drawing.

PREFERRED EMBODIMENT

Figure 1:
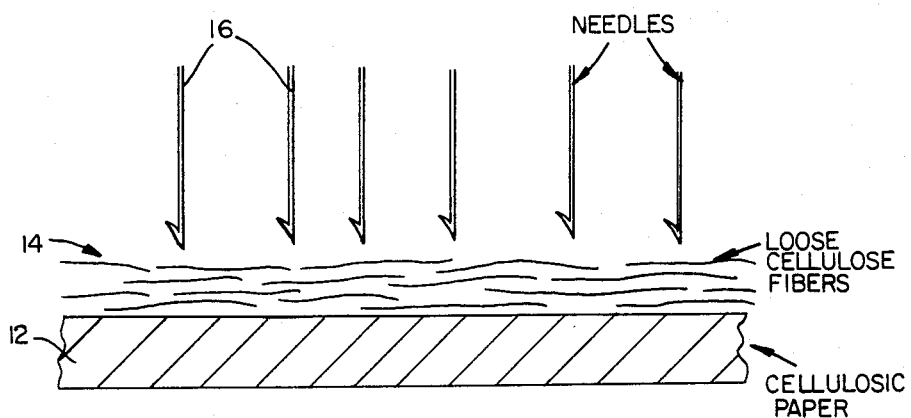
FIG. 1 is a greatly enlarged cross sectional view of the components of each web of the preferred embodiment of the invention prior to making it.

Referring to FIG. 1, in the preferred embodiment, a fiber faced web is to be formed by placing in position an elongated sheet of cellulosic paper 12 as a carrier and then arranging thereon loose synthetic fibers 14. The loose fibers are then passed through the carrier by needle-punching them, as by the needles 16, so the fibrous assume the position illustrated in FIG. 2, wherein the fibers protrude to either side of the paper and are held in position by the paper which then acts as a carrier. Preferably, the fiber 14 is made of celluose acetate. The paper carrier 12 is preferably that made by the Dexter Corporation of Windsor Locks, Conn., known as Dexter 193 which is made of cellulose and regenerated cellulose and is often used as sausage casing. The Dexter 193 carrier weighs 0.6 ounces per square yard, to which 0.9 to 1.2 ounces per square yard of the cellulose acetate fiber is added so as to bring the total weight of the paper web to 1.5 to 1.8 ounces per square yard. Another material which has also been found to be suitable for the carrier 12 is a light polypropylene scrim.

It should be appreciated that the fiber faced webs of the product invention need not be the unwoven needle punched webs of the preferred embodiment. The invention also envisions use of other materials such as simple non woven webs or even of woven napped materials. Additionally, the web material while advantageously using cellulose or cellulose acetate may also be produced from polypropylene, nylon, other suitable materials, or proper combinations of the aforementioned.

Figure 2:
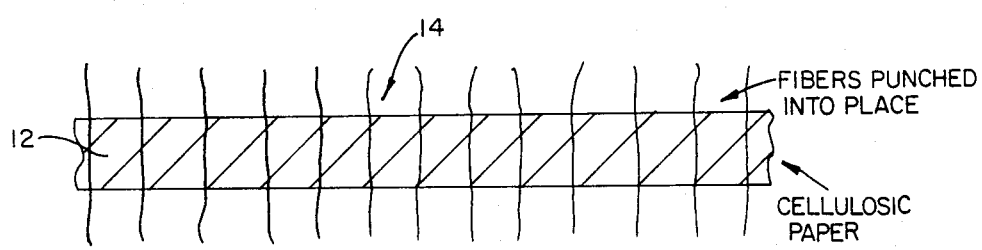
FIG. 2 is also a cross sectional view of the web of FIG. 1 after the web has been made.
Figure 3:
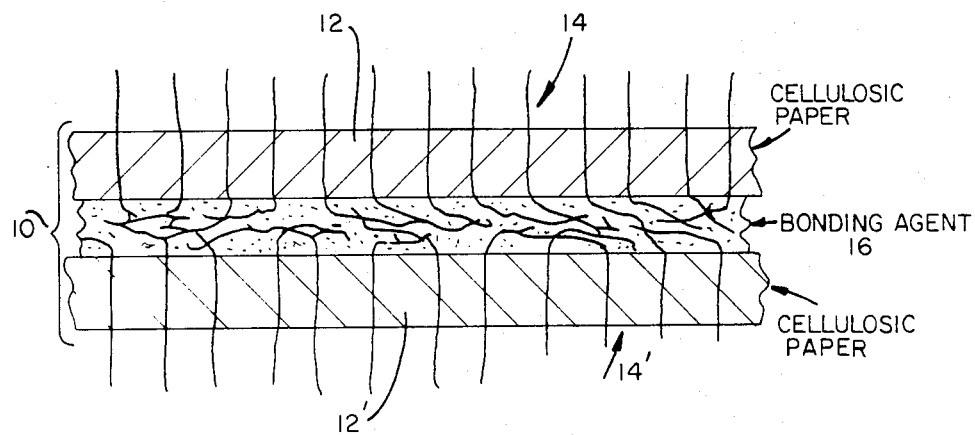
FIG. 3 is a cross sectional view of the adhesive device made from the webs illustrated in FIG. 2.

In FIG. 3 there is illustrated a new laminated adhesive device 10. The device 10 comprises a pair of fiber faced webs 12, 14 and 12', 14' made according to the product illustrated in FIG. 2. The web fibers are bonded together by the means of a thermoplastic bonding powder layer 16, as illustrated, to which a dry powder fixative may be optionally added as is more particularly described by the method disclosed hereinafter.

Figure 4:
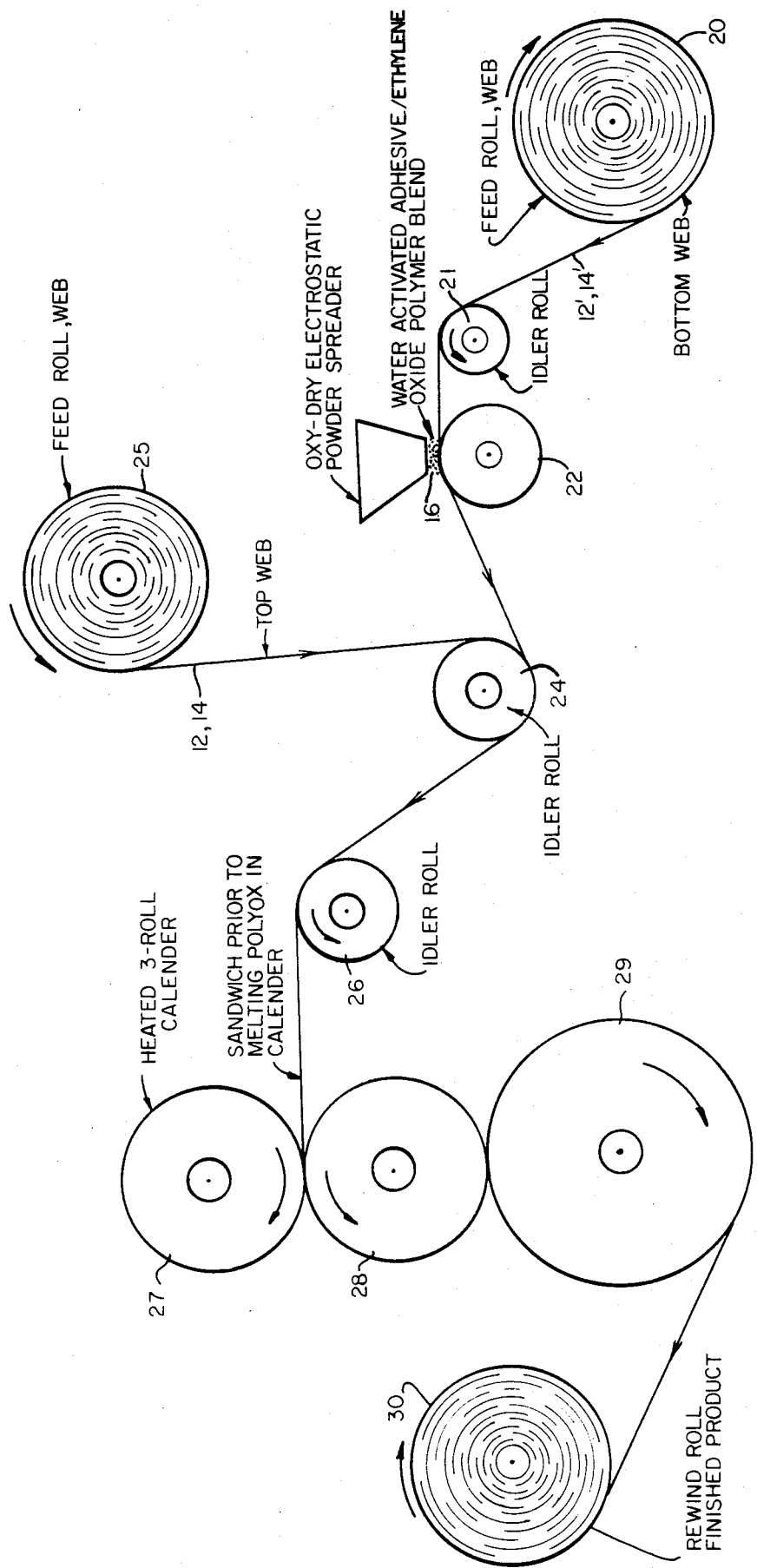
FIG. 4 is a schematic side view of the production equipment carrying out the novel method for producing the aforesaid new article of manufacture.

By referring to FIG. 4, the process for making the product may be more readily understood. Prior to the conducting of the hereinafter described method, fiber faced webs 12, 14 and 12', 14' may have been made and put up as a roll of material for use in the process. The web 12', 14' of FIG. 2 is fed from a roll 20 over an idler roll 21, horizontally over a guide roll 22 and under an electrostatic powder spreader 23 which progressively applies a bonding agent 16 of powdered ethylene oxide polymer in an even layer to the upper surface of said web 12', 14'. Meantime, the upper web 12, 14 of FIG. 2, is concurrently fed from a roll 25, under an idler roll 24 to be superimposed above and in contact with web 12', 14', so that the bonding agent 16 is therebetween. The superimposed webs are fed over an idler roll 26 and between a pair of calendar rolls 27, 28, heated to about 210° F., wherein the fibers of the webs 12, 14 and 12', 14' are bonded to the agent 16 into a unitary laminate which is withdrawn about a guide roll 29 and coiled up as at 30. In passing between the calendar rolls 27, 28, the ethylene polymer partially melts and deforms to bond the fibers 14, 14' in the carriers 12, 12' and to bond the webs together. No moisture is added other than that which is incidently present in the web or in the ethylene oxide polymer.

Figure 5:
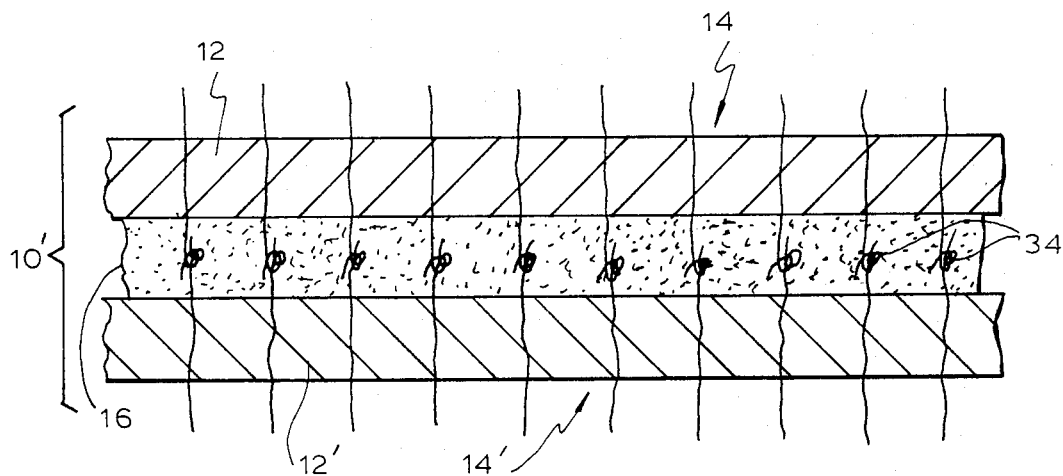
FIG. 5 is a cross sectional view, similar to FIG. 3 illustrating another embodiment of the adhesive device of the invention.
Figure 6:
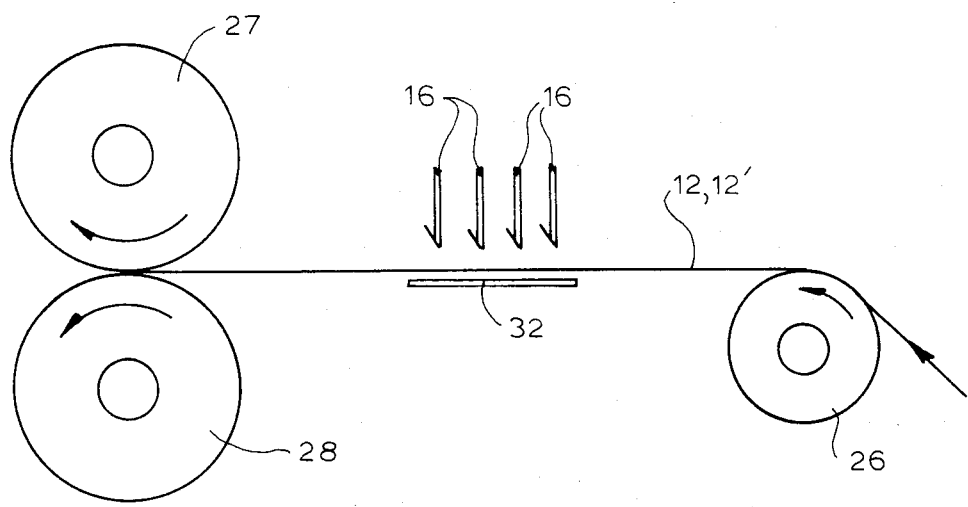
FIG. 6 is a schematic side view, similar to a portion of FIG. 4 of the production equipment carrying out the novel method for producing the embodiment illustrated in FIG. 5.

Refer now to FIGS. 5 and 6 for a description of another embodiment of the invention. It is noteworthy to explain that the invention illustrated in FIGS. 1-4, has met with excellent commercial acceptance and truly represented a significant advancement over the prior art known at the time of its conception and reduction to practice. The embodiment illustrated in FIGS. 5 and 6 represents still a further improvement over the invention illustrated in FIGS. 1-4. Specifically, by reason of the improvement about to be described, the end product indicated at 10' in FIG. 5 provides even greater resistance to delamination of the webs 12, 14, 12', 14' in the course of its use. Indeed, it can be said that the end product 10' exhibits a construction for which there is no significant likelihood of delamination even after extended periods of use.

As seen in FIG. 5, the construction of the embodiment 10' is somewhat similar to that of the earlier embodiment 10. However, an additional step in the earlier process of FIG. 4 is illustrated in new FIG. 6, according to which the synthetic fibers 14, 14' which had previously been passed through their respective carriers 12, 14' by needle-punching them, as by the needles 16, are again operated upon by the needles 16. This additional step preferably takes place in the process after the superimposed webs leave the idler roll 26 but before they reach the heated calendar rolls 27, 28. The advancing webs 12, 12' may be stopped, intermittently, to allow the needles 16 to punch into the superimposed webs 12, 12' against a suitable support platen 32. The needles reach into the region between the webs 12, 12' and entangle the respective ends of the fibers 14 and 14' such that they become mechanically interwined or interlocked as indicated at 34 (FIG. 5).

Although this additional step has been disclosed as occurring after the webs 12, 12' have left the idler roll 26 and before they reach the heated calendar rolls 27, 28, it will be understood that it might also take place simultaneously with the heat bonding, or subsequent thereto, but prior to the web being wound onto the take-up roll 30.

The product of the process described is soft to the touch and when shaped in a known manner and placed between a dental prosthetic plate and the gum, after wetting, becomes a durable adhesive to bind the prosthetic to the gum. The ethylene oxide polymer's thermoplastic characteristics cause the dental laminate to hold together longer than the fiber types described in the prior art and the water activated adhesive characteristic helps the dental adhesive form a gel-like adhesive mass which maintains a most advantageous position in the mouth to effectively operate. Moreover, the bulk and flexibility of the laminate acts to cushion and assist in the uniform holding power of the device. As seen above, the ethylene oxide polymer is used both to thermoplastically bind the fibrous webs and to provide a wet denture adhesive seal.

Additionally, dry water-activated adhesives may be advantageously employed in conjunction with the ethylene oxide polymer. Thus, in the process for making the product, the electrostatic powder spreader 23 progressively applies in an even layer to the upper surface of web 12', 14' an admixture of the binding agent, powdered ethylene oxide polymer, to which there has been added a powdered dry water-activated adhesive. When the upper web 12, 14 is fed under the idler roll 24 and into contact with 12', 14', the ethylene-oxide polymer/water-activated adhesive powder is therebetween. By passing through the heated calander rolls 27, 28, the ethylene oxide polymer thermoplastically bonds the webs and in addition causes the uniformly distributed dry water-activated adhesive to be fixed in position in the laminate. The water-activated adhesive does not become part of the bond and no other bonding agents of any kind are employed. In this manner, after wetting, the product of the process described becomes a desirable adhesive which forms a durable seal between the denture and the gums. Due to the thermoplastic bonding, it holds together longer than the fiber types described in the prior art. Moreover, the product achieved by the additional needling step increases the certainty of holding together during use. Additionally, it better retains the water-activated adhesive, which together with the ethylene oxide polymer, keeps the dental adhesive and hence the denture plate in position.

The water-activated adhesive may be any of many well-known adhesives, and preferably comprises from 0% to approximately 90%, by weight, of the ethylene oxide polymer/water-activated adhesive mixture. Sodium alginate has been used as the water-activated adhesive with much success. Additionally, materials such as cellulose gum, sodium carboxy methyl cellulose, methyl cellulose, polyvinyl methyl ether maleate, geletin, pectin and tragacanth, among others, can each be used as the adhesive in combination with the sodium alginate or in its stead. Of course, suitable combinations of the adhesives may also be used.

Referring to the process illustrated in FIG. 4, in the preferred embodiment the bonding agent 16, ethylene oxide polymer powder, was admixed with sodium alginate and spread between the two webs in a 50—50 weight blend of Kelvis-brand sodium alginate and polyox WSR-205 ethylene oxide polymer. This blend was prepared in a stainless steel ribbon mixer. The blending was applied to the bottom web 12', 14' by passing the web under an Oxy-Dry electrostatic powder spreader filled with the aforesaid alginate/polyox powder. A uniform layer was spread as evenly as possible. Most of the powder laid on the surface of the web. The quantity of the alginate/polyox powder spread on the web was closely controlled, at 1.5 ounces of the powder per square yard of the web.

Ethylene oxide polymer powder was also admixed with a mixture of polyvinyl methyl ether-maleate and pectin. The ethylene oxide powder was 15% by weight, the polyvinyl methyl ether-maleate 65% and pectin 20% by weight. The blend was applied to the top of web 12', 14' by passing it under an Oxy-Dry electrostatic powder spreader filled with the aforesaid polyvinyl methyl ether-maleate/pectin/ethylene oxide polymer powder. A uniform layer was spread as evenly as possible and the spread was closely controlled at 1.5 ounces of the powder per square yard of the web.

Ethylene oxide powder was also admixed with a mixture of sodium alginate and methyl cellulose. The chemicals had weight percentages respectively of 65, 15 and 20. The blend was uniformly spread by the Oxy-Dry electrostatic powder spreader to the top of web 12', 14', and was closely controlled at 1.5 ounces of powder per square yard of the web. In another run, 1.5 ounces of ethylene oxide polymer powder per square yard of the web was uniformly spread to the top of web 12', 14'.

In all of the above examples, web 12, 14 was fed from a roll 25, under an idler roll 24 and superimposed above and in contact with web 12', 14' with the powder in between. The superimposed webs were fed over idler roll 20 and between heated cylinder rolls 27 and 28 to deform the thermoplastic ethylene oxide polymer by heat and pressure, and to form the resulting products.

The weight of the resulting product of the examples discussed above were 5.1 ounces per square yard, with reasonable tolerances. Of this, 3.6 ounces were the webs (two pieces at 1.8 ounces each), and 1.5 ounces was ethylene oxide polymer or the water-activated adhesive/ethylene oxide polymer blend. The thickness of the products was about 0.015 to 0.018 inches. The temperature of the heated calander rolls 27, 28 was approximately 210° F., which was sufficient to melt the ethylene oxide polymer, but low enough to not affect or soften the web or the water-activated adhesives. The resulting products were dental adhesive laminates with excellent characteristics. The products held together longer than the previous products of the prior art, and the products better retained the water-activated adhesives so as to permit the dental adhesion products to more effectively operate.

As presently produced, the product is 45 inches wide, then slit to 22½ inches wide for convenient handling. Typically, the product is rolled up on cores for shipment. No drying or other processing is conducted, nor are other chemicals added. The rollgoods are thereafter die-cut into the appropriate shapes for use as dental adhesives and packed for sale.

Although a preferred embodiment and other examples of the process and product thereof have been described, it will be evident that changes may be made in the steps of the process and components and details of the product without departing from the spirit and principles of the inventions.

What is claimed:

1. A new dental adhesive product comprising a laminate of superimposd fiber faced webs, each web having a carrier portion with fibers held therein and protruding therefrom to present a fiber facing on each side of each of said webs, the fibers of one face of one of said webs being dry heat bonded to the fibers of an opposing face of the other of said webs by thermoplastic ethylene oxide polymer located between said webs, said ethylene oxide polymer having been deformed by the application of dry heat and pressure whereby the ethylene oxide polymer both bonds said webs and is available to the user as a dental fixative.

2. A dental adhesive product according to claim 1 in which a dry water-activated adhesive is also present between said webs to increase the fixative ability of the product.

3. A dental adhesive product according to claim 2 in which said dry water-activated adhesive is sodium alginate.

4. The method of producing a dental adhesive product which comprises, applying a dry thermoplastic ethylene oxide polymer to a surface of a first fibrous web, contacting said first web with a second fibrous web in superimposed relation, and applying pressure and dry heat to deform the ethylene oxide polymer and thereby thermoplastically bond the webs into a unitary structure.

5. A method according to claim 4 in which a dry water-activated adhesive powder is admixed with the dry ethylene oxide polymer and is applied to the first web prior to contacting the first web with a second fibrous web.

6. A new dental adhesive product comprising a laminate of superimposed webs, each web having a carrier portion with synthetic fibers held therein and protruding therefrom to present a fiber facing on each side of each of said webs such that said fibers of each of said respective webs are caused to intermingle in the region between said webs, said fibers of said webs being dry heat bonded to each other by thermoplastic ethylene oxide polymer located between said webs, said ethylene oxide polymer having been deformed by the application of dry heat and pressure whereby the ethylene oxide polymer both bonds said webs and is available to the user as a dental fixative.

7. A dental adhesive product according to claim 6 in which a dry water-activated adhesive is also present between said webs to increase the fixative ability of the product.

8. A dental adhesive product according to claim 7 in which said dry water-activated adhesive is sodium alginate.

9. The method of producing a dental adhesive product which comprises inserting a plurality of synthetic fibers into first and second fibrous webs so that the fibers extend transversely through the webs, applying a dry thermoplastic ethylene oxide polymer to a surface of the first web, contacting the first web with the second web in superimposed relation, and applying pressure and dry heat to deform the ethylene oxide polymer and thereby thermoplastically bond the webs and the fibers into a unitary structure.

10. A method according to claim 9 in which a dry water-activated adhesive powder is admixed with the dry ethylene oxide polymer and is applied to the first web prior to contacting the first web with a second fibrous web.

11. A new dental adhesive product comprising a laminate of superimposed webs, each web having fibers held therein and protruding therefrom to present a fiber facing on each side of each of said webs such that said fibers of each of said respective webs are intermingled and entangled so as to be mechanically interlocked in the region between said webs, said fibers of said webs being dry heat bonded to each other by thermoplastic ethylene oxide polymer located between said webs, said ethylene oxide polymer having been deformed by the application of dry heat and pressure whereby the ethylene oxide polymer both bonds said webs and is available to the user as a dental fixative.

12. A new dental adhesive product comprising a laminate of superimposed webs, each web having a carrier portion with fibers held therein and protruding therefrom to present a fiber facing on each side of each of said webs such that said fibers of each of said respective webs are intermingled and entangled so as to be mechanically interlocked in the region between said webs, said fibers of said webs being dry heat bonded to each other by thermoplastic ethylene oxide polymer located between said webs, said ethylene oxide polymer having been deformed by the application of dry heat and pressure whereby the ethylene oxide polymer both bonds said webs and becomes a dental fixative in use in a wearer's mouth.

13. A dental adhesive product according to claim 12 in which a second dry but water-activated adhesive is also present between said webs to increase the fixative ability of the product.

14. A dental adhesive product according to claim 13 in which said dry water-activated adhesive is sodium alginate.

15. The method of producing a dental adhesive product which comprises, inserting a plurality of synthetic fibers into first and second fibrous webs so that the fibers extend transversely through the webs, entangling the respective ends of the fibers extending from the first web with those extending from the second web so that the respective ends become mechanically interlocked, applying a dry thermoplastic ethylene oxide polymer to a surface of the first web, contacting the first web with the second web in superimposed relation, and applying pressure and dry heat to deform the ethylene oxide polymer and thereby thermoplastically bond the webs and the fibers into a unitary structure.

16. A method according to claim 15 in which a dry water-activated adhesive powder is admixed with the dry ethylene oxide polymer and is applied to the first web prior to contacting the first web with a second fibrous web.

17. A new dental adhesive product according to any one of claims 1, 6, and 12 in which at least one of said carrier portions is cellulose paper and said protruding fibers in at least one of said carriers are cellulose acetate.

* * * * *